United States Patent
Lee

(10) Patent No.: US 12,070,247 B2
(45) Date of Patent: Aug. 27, 2024

(54) UTERINE MANIPULATOR

(71) Applicant: ORANGE MEDICS, INC., Daejeon (KR)

(72) Inventor: Ki Hwan Lee, Daejeon (KR)

(73) Assignee: ORANGE MEDICS, INC, Daejeon (KR)

( * ) Notice: Subject to any disclaimer, the term of this patent is extended or adjusted under 35 U.S.C. 154(b) by 1037 days.

(21) Appl. No.: 16/975,719

(22) PCT Filed: Mar. 7, 2019

(86) PCT No.: PCT/KR2019/002630
§ 371 (c)(1),
(2) Date: Aug. 26, 2020

(87) PCT Pub. No.: WO2019/172664
PCT Pub. Date: Sep. 12, 2019

(65) Prior Publication Data
US 2021/0000507 A1   Jan. 7, 2021

(30) Foreign Application Priority Data

Mar. 9, 2018 (KR) .......................... 10-2018-0027975
Nov. 27, 2018 (KR) .......................... 30-2018-0055255

(51) Int. Cl.
*A61B 17/42* (2006.01)
*A61B 17/00* (2006.01)
*A61B 17/34* (2006.01)

(52) U.S. Cl.
CPC ................ *A61B 17/4241* (2013.01); *A61B 2017/00314* (2013.01); *A61B 2017/00367* (2013.01); *A61B 2017/0042* (2013.01); *A61B 2017/00544* (2013.01); *A61B 2017/00557* (2013.01); *A61B 2017/3419* (2013.01); *A61B 2017/4225* (2013.01)

(58) Field of Classification Search
CPC .................... A61B 17/4241; A61B 2017/4225
See application file for complete search history.

(56) References Cited

U.S. PATENT DOCUMENTS

| | | | |
|---|---|---|---|
| 4,016,867 | A | 4/1977 | King et al. |
| 5,643,285 | A | 7/1997 | Rowden et al. |
| 2007/0142752 | A1 | 6/2007 | Kotmel et al. |
| 2011/0130769 | A1 | 6/2011 | Boebel et al. |
| 2016/0270819 | A1 | 9/2016 | Ahluwalia et al. |

FOREIGN PATENT DOCUMENTS

EP    2116202 A1   11/2009

OTHER PUBLICATIONS

International Search Report for PCT/KR2019/002630 mailed Jun. 12, 2019 from Korean Intellectual Property Office.

*Primary Examiner* — Christine H Matthews
(74) *Attorney, Agent, or Firm* — Revolution IP, PLLC

(57) ABSTRACT

A uterine manipulator includes: a main body coupled at one end thereof to a handle and extending in one direction to be inserted into the vagina; a mount coupled to the other end of the main body and having a guide hole formed therethrough in a longitudinal direction of the main body; a support disposed on the mount to support the uterine cervix; a slider inserted into the guide hole to be coupled at one end thereof to the main body and extending in one direction to be inserted into the uterine corpus; an adjuster coupled to both the one end of the slider and the main body; and a head disposed at the other end of the slider.

2 Claims, 11 Drawing Sheets

[FIG. 1]
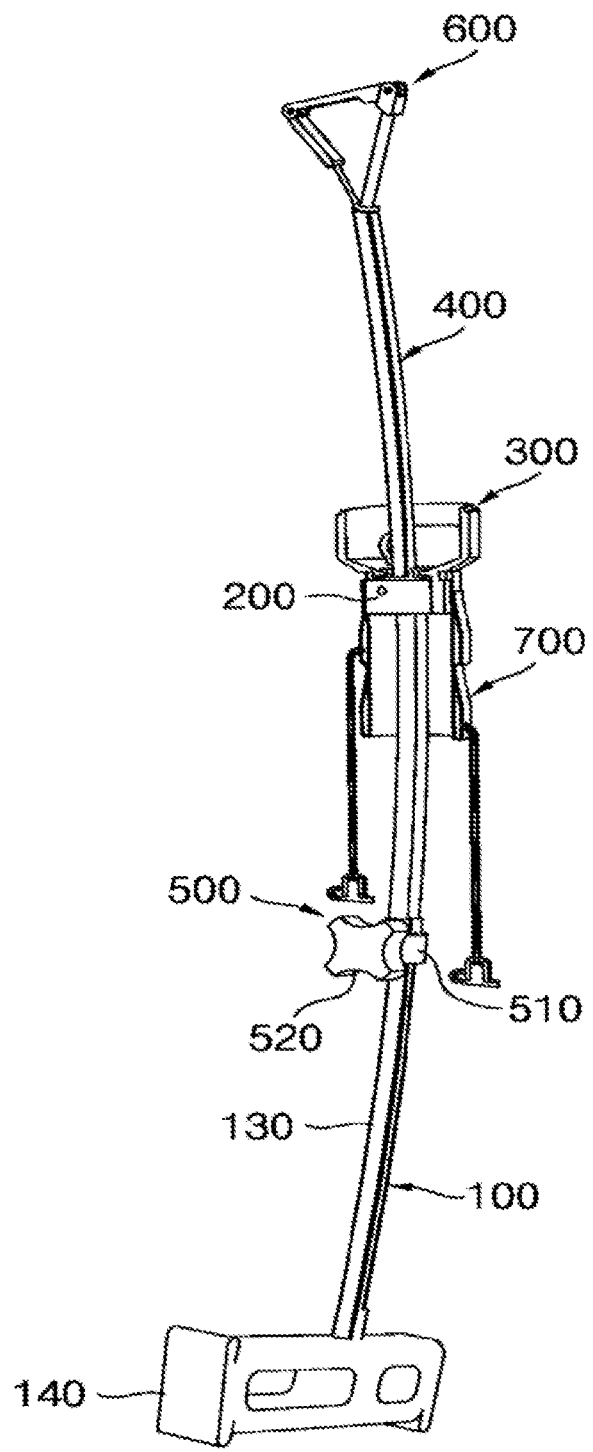

[FIG. 2]
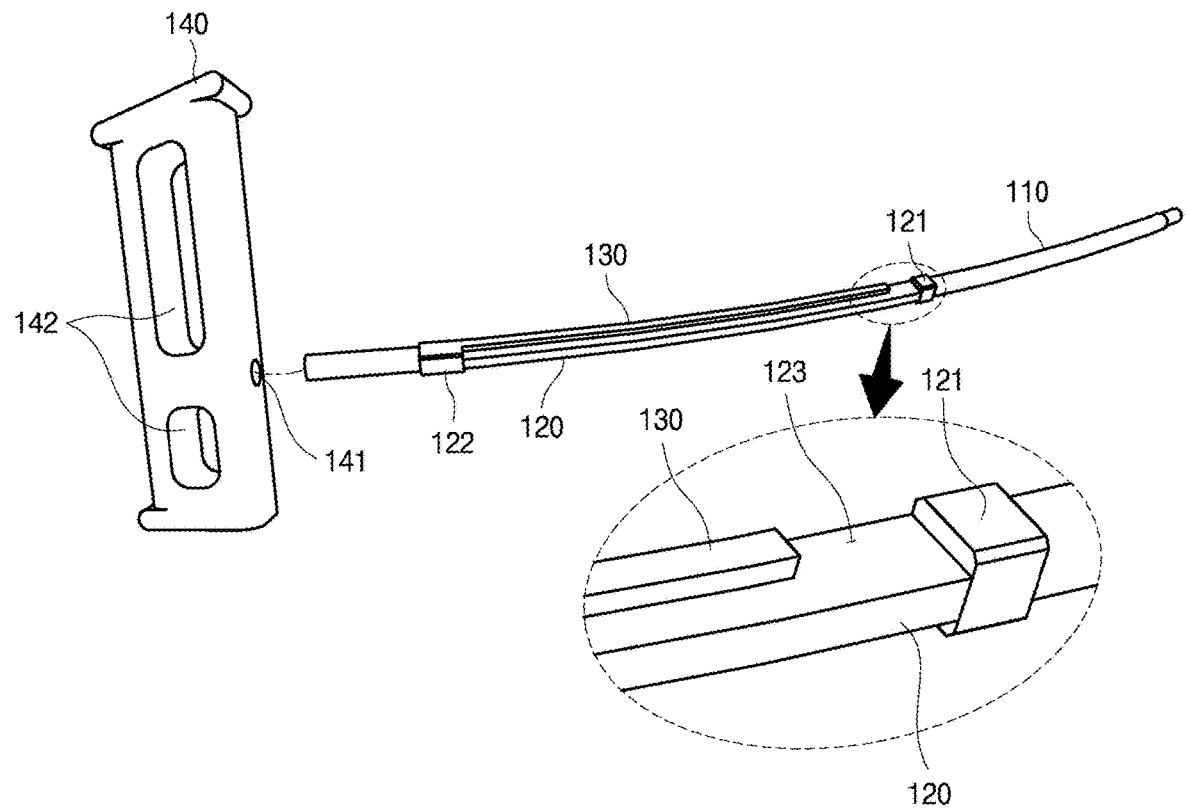
[FIG. 3]
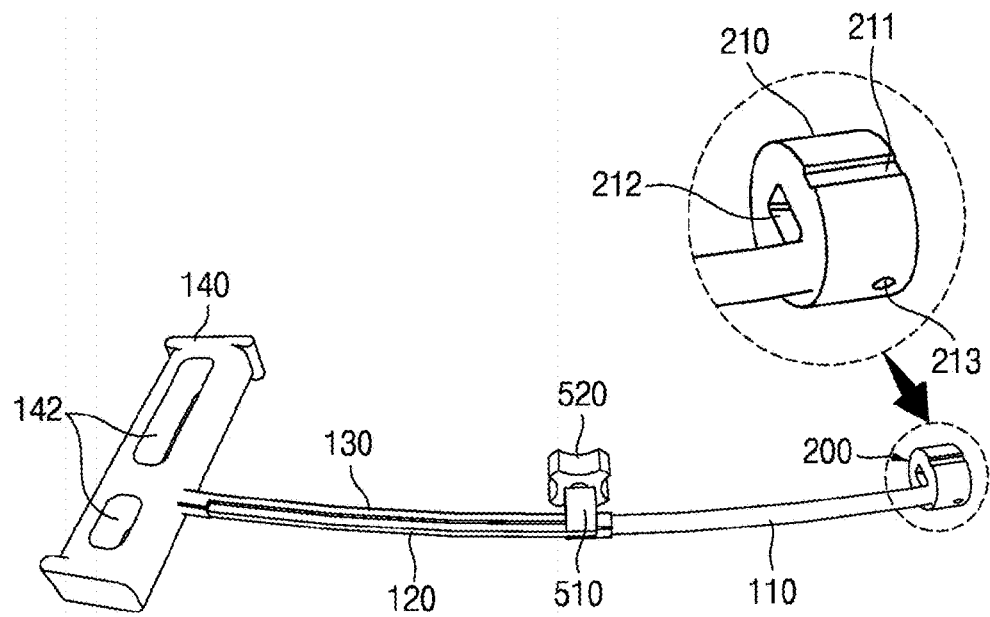

[FIG. 4]
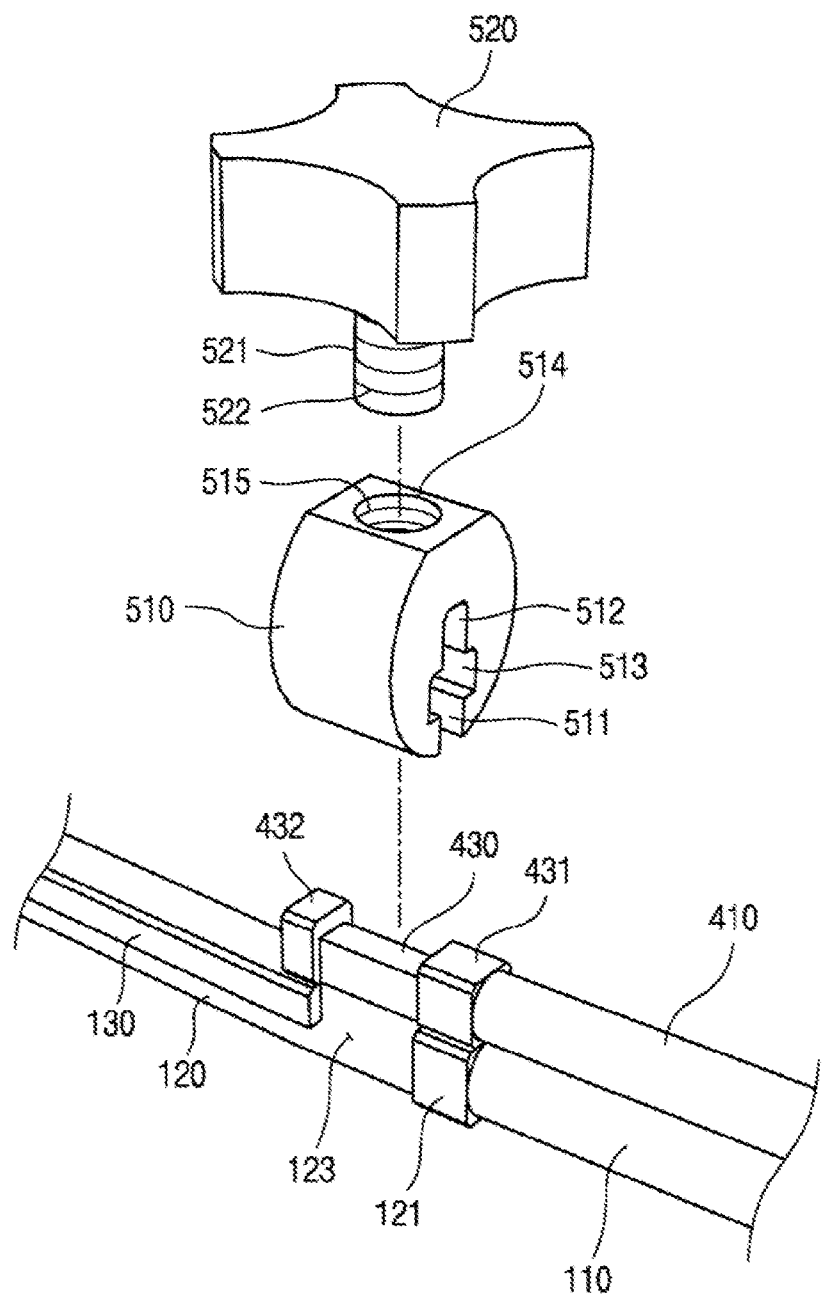

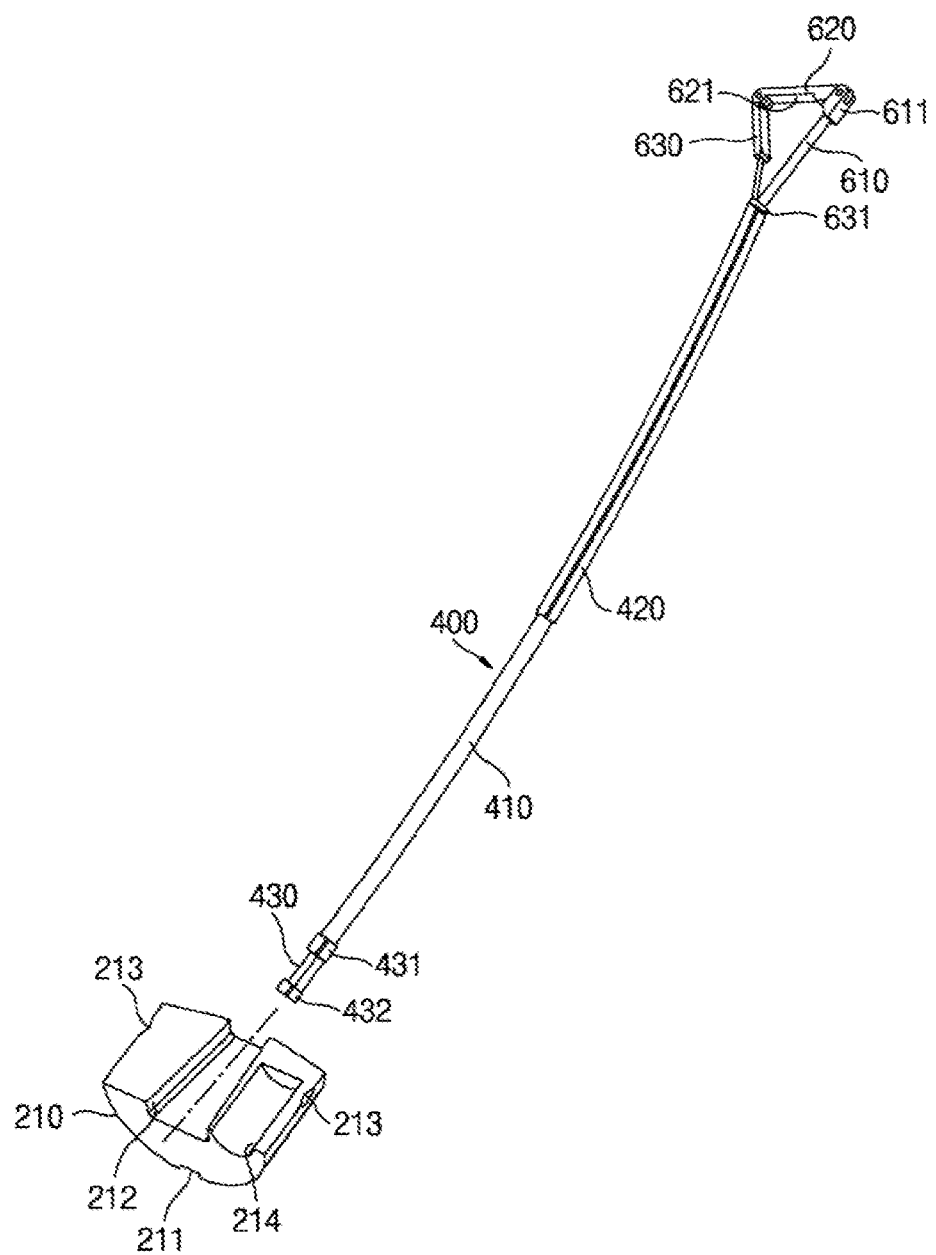
[FIG. 5]

[FIG. 6]
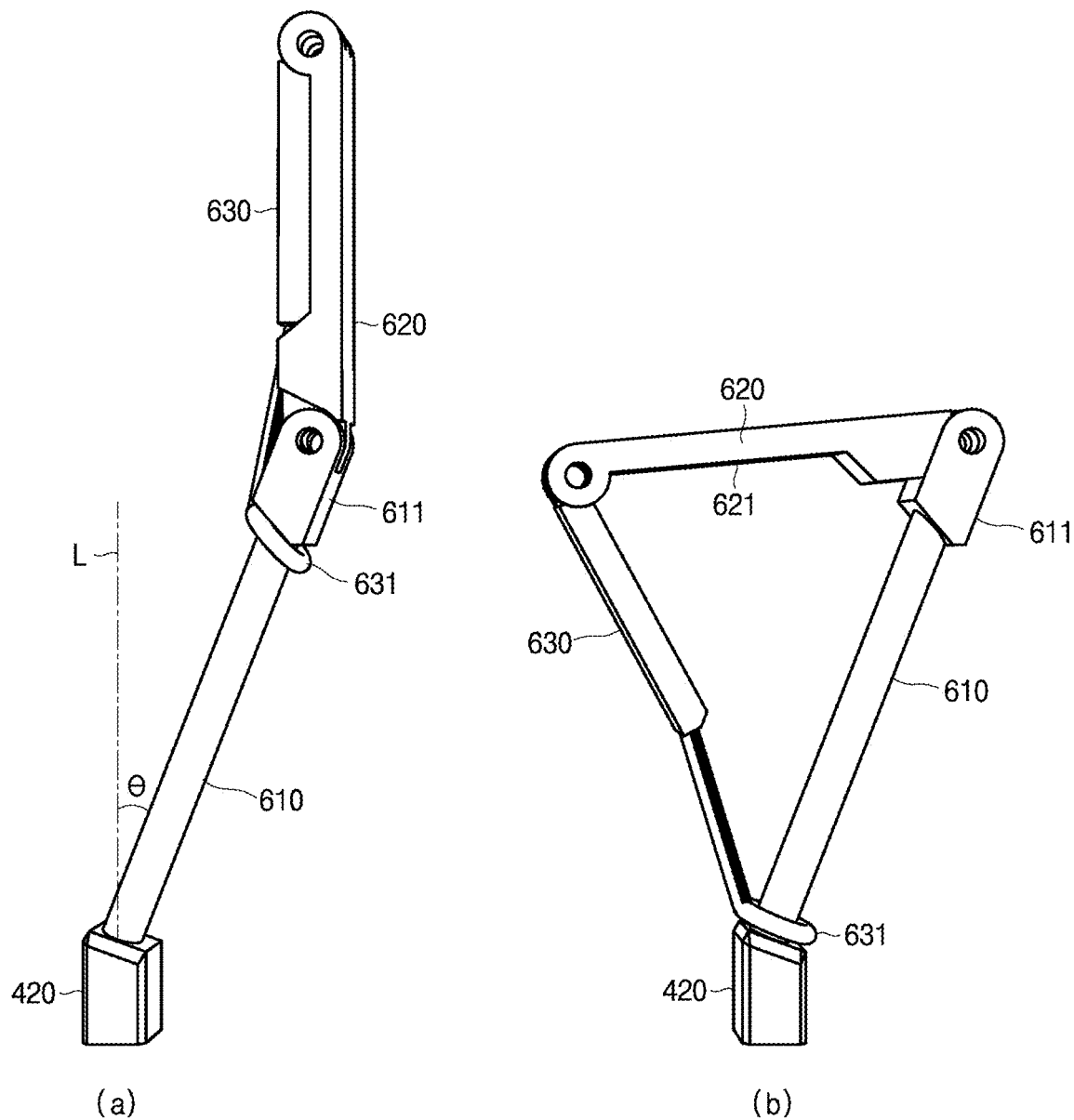
(a) (b)

[FIG. 7]
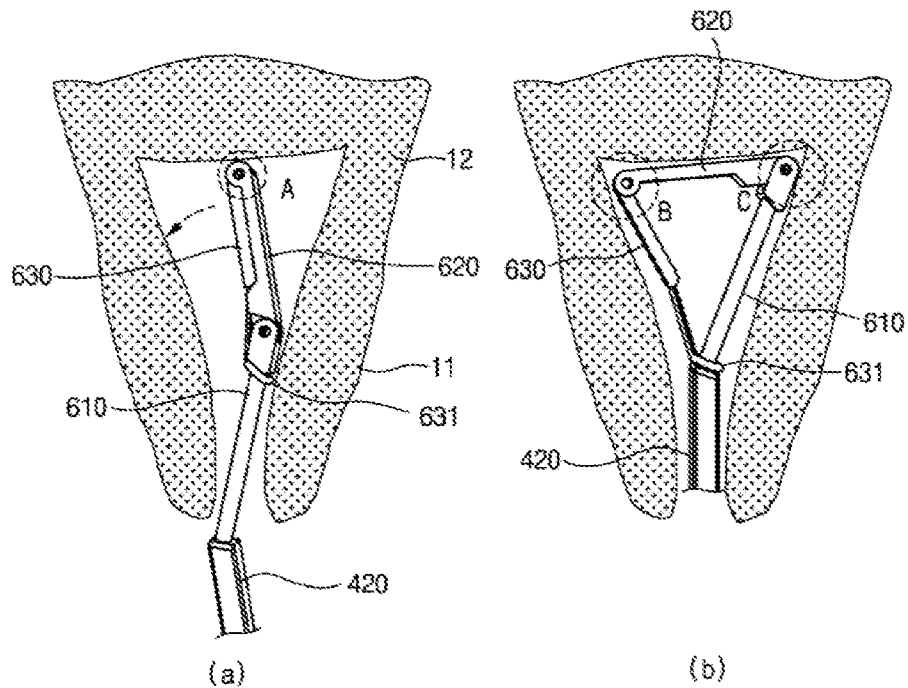
[FIG. 8]
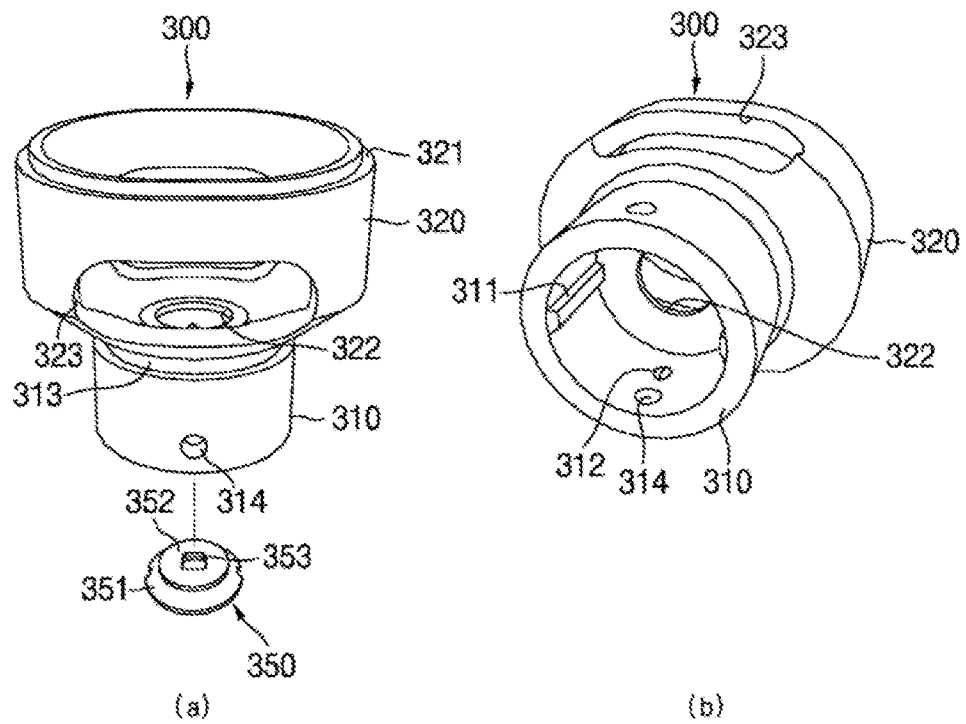

[FIG. 9]
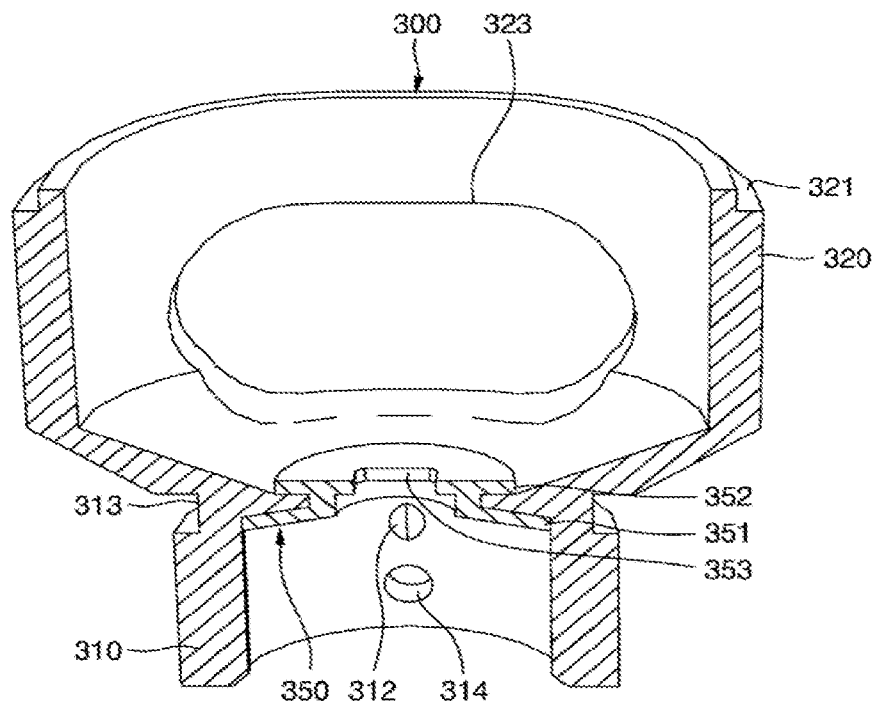
[FIG. 10]
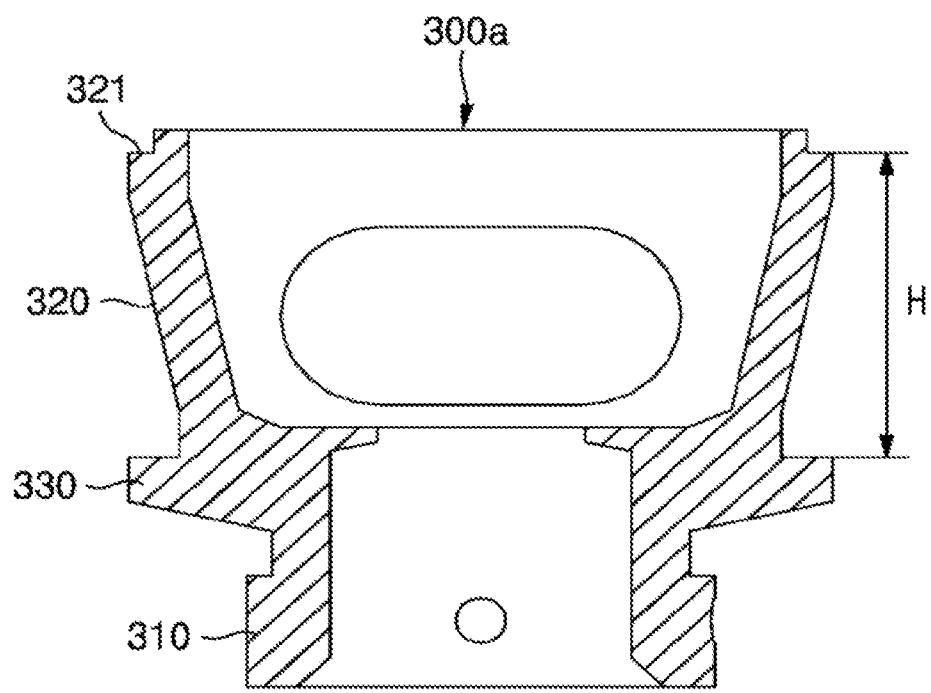

[FIG. 11]
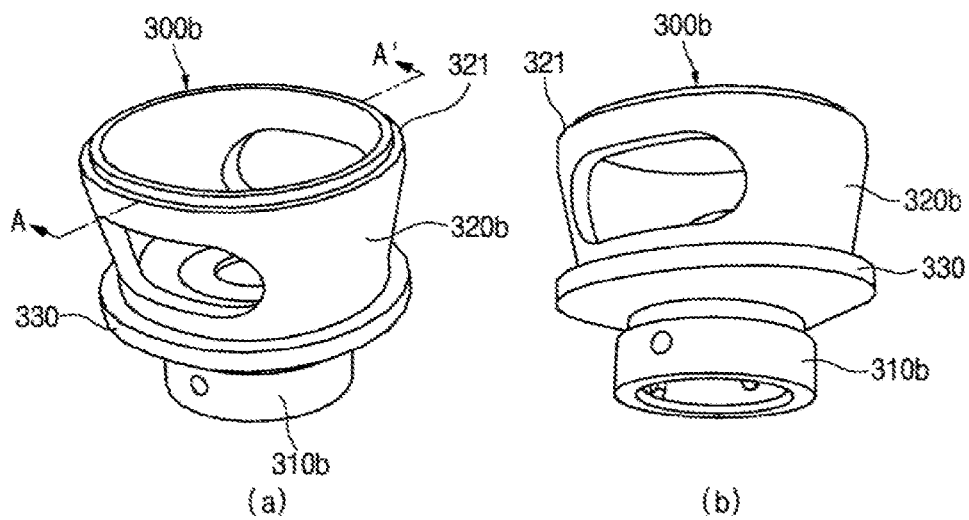
[FIG. 12]
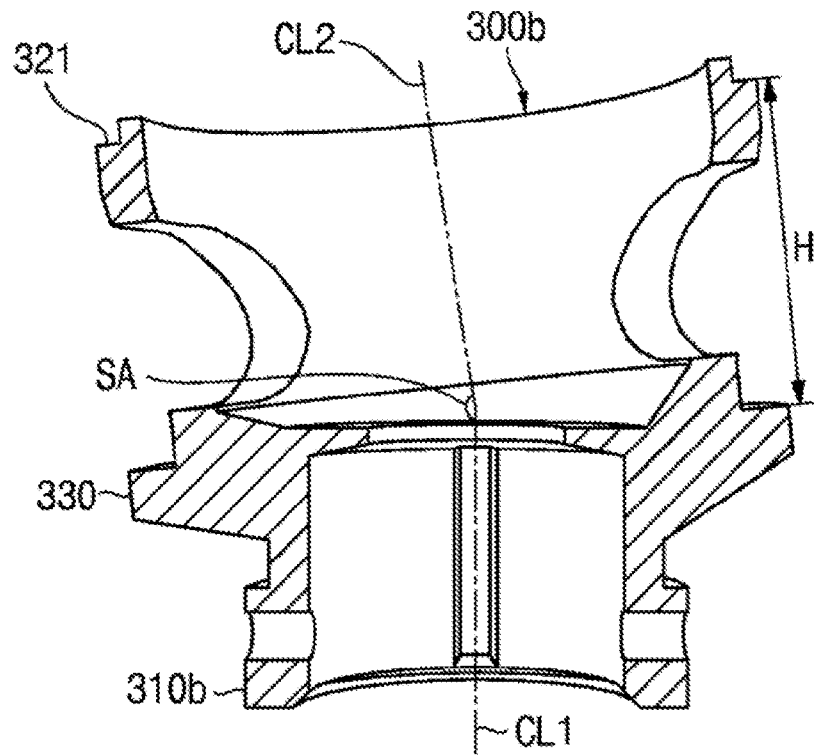

[FIG. 13]
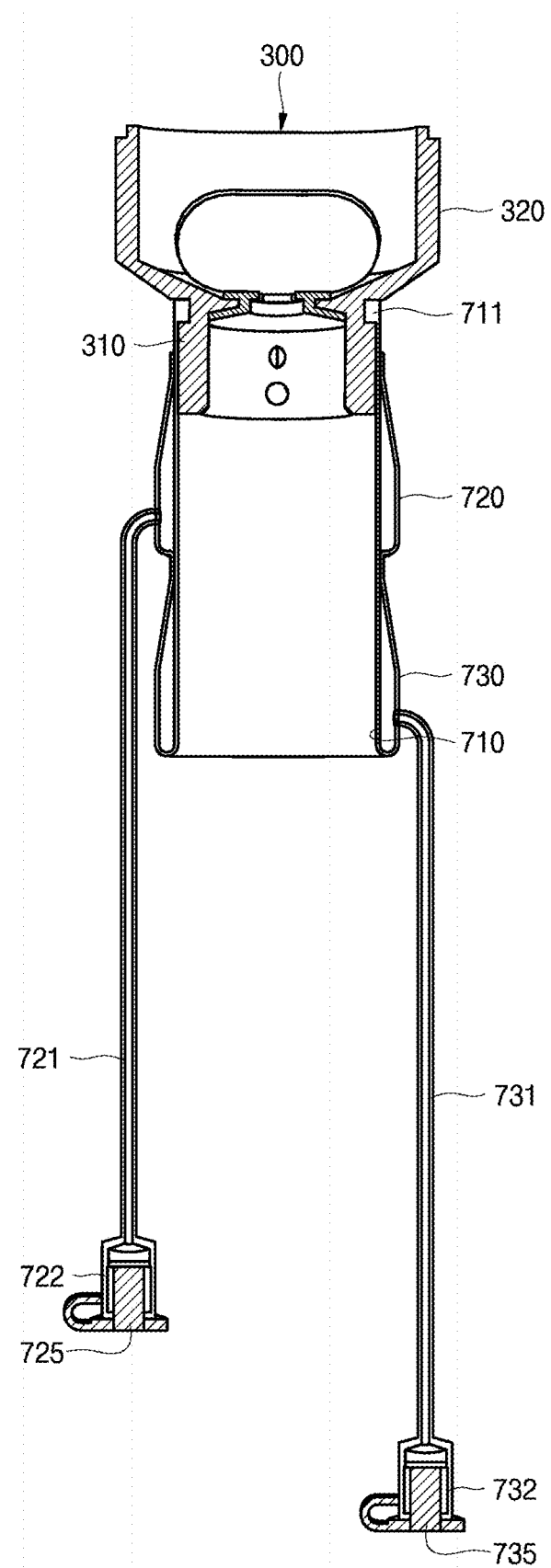

[FIG. 14]
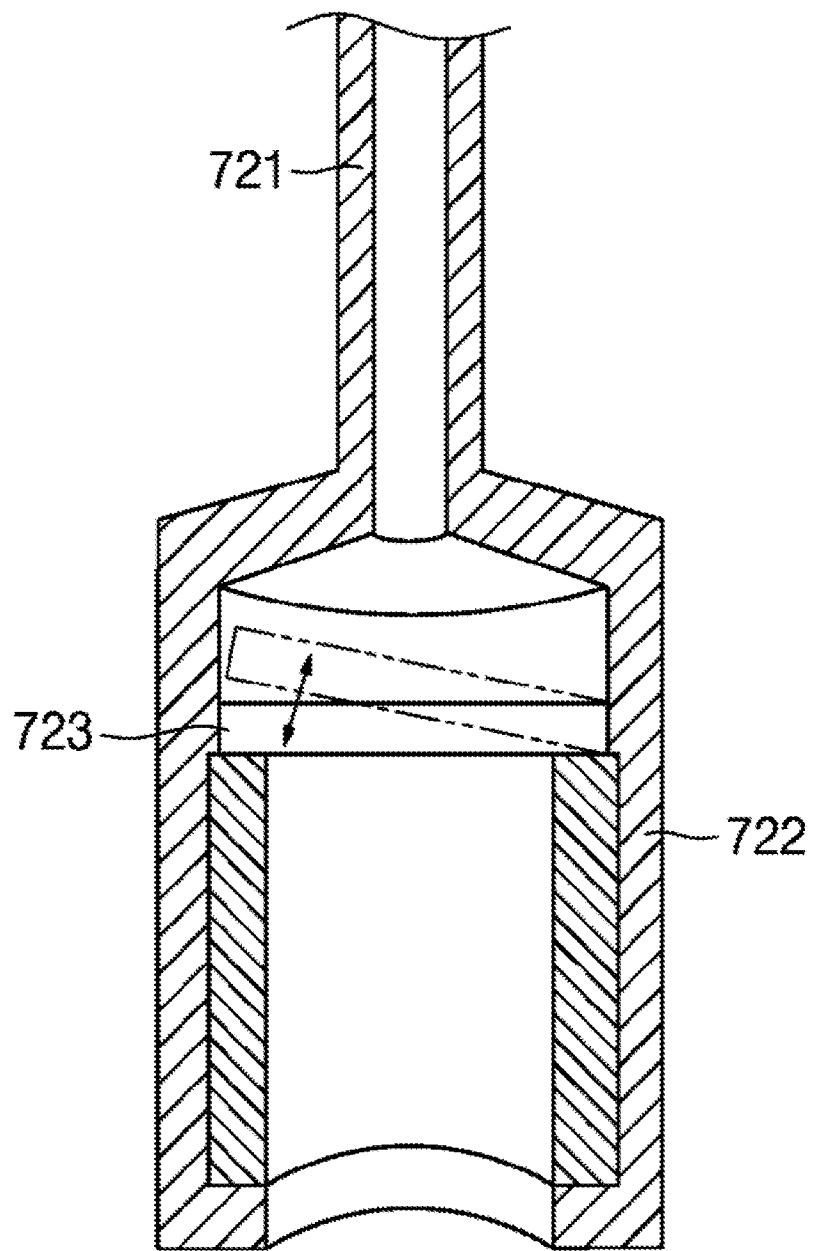

【FIG. 15】
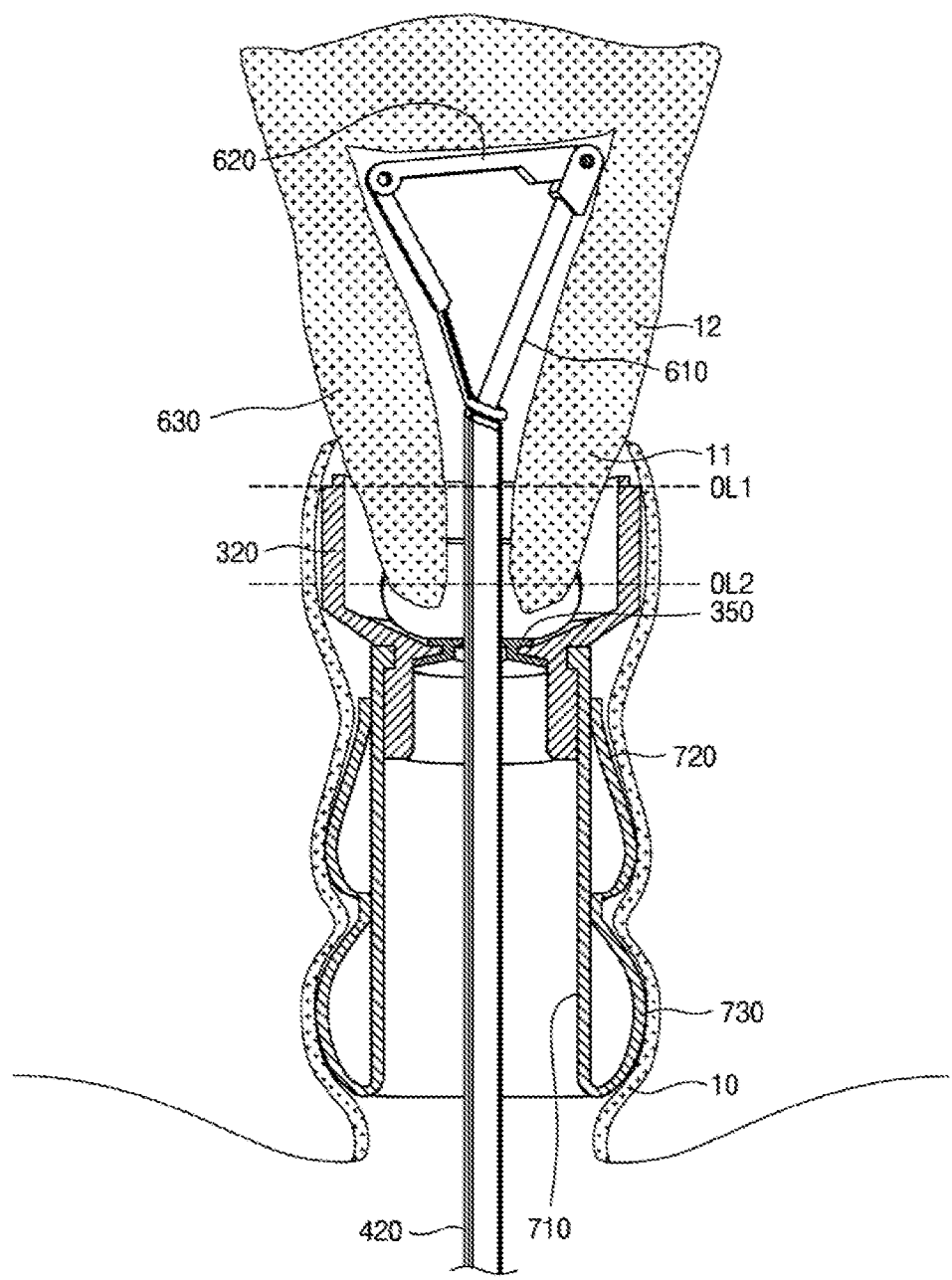

UTERINE MANIPULATOR

TECHNICAL FIELD

The present invention relates to a uterine manipulator, and, more particularly, to a uterine manipulator which can easily manipulate the uterus in laparoscopic surgery.

BACKGROUND ART

Hysterectomy is the most common form of gynecologic surgery. In the past, abdominal hysterectomy using an incision in the abdomen was generally performed, whereas, recently, laparoscopic hysterectomy has been most widely performed.

Laparoscopic surgery has several advantages over abdominal surgery. In terms of technology, laparoscopic surgery allows close anatomical/pathological examination of a target organ and easy access to the vagina or the rectum during surgery. In addition, laparoscopic surgery can reduce the risk of intestinal adhesion by preventing organs in the abdominal cavity from being exposed to the atmosphere. In terms of benefit for patients, laparoscopic surgery allows less pain due to smaller incision, better cosmetic results, shorter hospital stay due to less pain, quicker return to everyday life, less infection, a lower risk of intestinal obstruction, and less bleeding than abdominal surgery.

Recently, laparoscopic surgery is also performed for uterine cervical cancer. In hysterectomy and myomectomy, manipulation of the uterus is essential for successful surgery, and a uterine manipulator is used as an essential instrument for laparoscopic surgery in the field of gynecology.

A uterine manipulator can shorten operation time in laparoscopic surgery by facilitating manipulation of the uterus. However, despite being capable of manipulating the uterus front and back and side to side, typical uterine manipulators cannot rotate the uterus, and thus do not ensure efficient surgery.

DISCLOSURE

Technical Problem

Embodiments of the present invention have been conceived to overcome such a problem in the art and it is an aspect of the present invention to provide a uterine manipulator which can easily manipulate the uterus in laparoscopic surgery.

The above and other aspects of the present invention will become apparent to those skilled in the art from the detailed description of the following embodiments in conjunction with the accompanying drawings.

Technical Solution

In accordance with an aspect of the present invention, there is provided a uterine manipulator adapted to be inserted into a woman's vagina and the uterine cervix and the uterine corpus connected to the vagina to manipulate the uterus in laparoscopic surgery, the uterine manipulator including: a main body coupled at one end thereof to a handle and extending in one direction to be inserted into the vagina; a mount coupled to the other end of the main body and having a guide hole formed therethrough in a longitudinal direction of the main body; a support disposed on the mount to support the uterine cervix; a slider inserted into the guide hole to be coupled at one end thereof to the main body and extending in one direction to be inserted into the uterine corpus; an adjuster coupled to both the one end of the slider and the main body, moved back and forth in the longitudinal direction of the main body to move the slider back and forth in the longitudinal direction of the main body, and securing the slider to the main body to adjust a length of the slider relative to the main body; a head disposed at the other end of the slider, the head being adapted to be changed into an inverted triangle shape corresponding to a shape of a lower portion of the uterus inside the uterine corpus by being pressed by an upper portion of the uterine corpus upon insertion of the slider into the uterine corpus and being adapted to be returned to a shape that the head has upon insertion into the uterine corpus by being pressed by the uterine cervix upon withdrawal of the slider from the uterine corpus; and an airbag coupled to the support and inflated with air supplied thereinto to seal an inside of the vagina.

In one embodiment of the present invention, the main body may include: a first stick forming a body of the main body; a first guide extending to a predetermined length from the first stick in a longitudinal direction of the first stick and having a rectangular cross-section, the first guide including a first stopper protruding from one end thereof and a second stopper protruding from the other end thereof; and a guide rail extending on both side surfaces of the first guide in a longitudinal direction of the first guide, connected at one end thereof to the second stopper, and separated at the other end thereof from the first stopper to form an insertion groove between the other end thereof and the first stopper.

In one embodiment of the present invention, the slider may include: a second stick extending in one direction; a second guide connected to one end of the second stick, extending to a predetermined length in one direction, and having a rectangular cross-section; and a securing portion formed at the other end of the second stick and corresponding in cross-section to the first guide, the securing portion including a third stopper protruding from one end thereof to correspond to the first stopper and a fourth stopper protruding from the other end thereof, the securing portion being continuous with the insertion groove.

In one embodiment of the present invention, the adjuster may include: a sliding block having a first slit corresponding in cross-section to the first guide to receive the first guide therein, a second slit extending from the first slit and corresponding in cross-section to the securing portion to receive the securing portion therein, and a third slit formed at both sides of an inner surface of the first slit and corresponding in cross-section to the guide rail to receive the guide rail therein, the sliding block being moved back and forth along the first guide to move the slider; and an adjustment lever inserted into an engagement hole formed through the sliding block to be connected to the second slit and pushing the securing portion to secure the slider.

In one embodiment of the present invention, the mount may include: a body block having a coupling groove axially formed on one surface thereof to receive the one end of the first stick therein; a pair of long grooves axially formed on an outer surface of the body block; the guide hole being axially formed through the body block and corresponding in cross-section to the second guide to guide movement of the slider while restraining rotation of the slider; and a pair of recesses formed on the outer surface of the body block.

In one embodiment of the present invention, the guide hole may be enlarged in a direction from the mount to the handle.

In one embodiment of the present invention, the support may include: a coupling cap formed on an inner surface thereof with a pair of long protrusions corresponding to the pair of long grooves and a pair of coupling protrusions corresponding to the pair of recesses to be coupled to the body block, the coupling cap having a mounting groove circumferentially formed on an outer surface thereof and a cup connected to the coupling cap and adapted to receive the uterine cervix therein.

In one embodiment of the present invention, the coupling cap may be formed therethrough with a coupling hole to which a tenaculum is coupled, the cup may have a stepped portion circumferentially formed at an upper portion thereof and having a uniform height.

In one embodiment of the present invention, the cup may be higher at a rear portion thereof than at a front portion thereof such that the upper portion of the cup is inclined forward.

In one embodiment of the present invention, the cup may further have a guide ring circumferentially protruding from a lower outer surface thereof.

In one embodiment of the present invention, the guide ring may be separated a distance of 1.5 cm to 2.5 cm from the stepped portion.

In one embodiment of the present invention, the cup may have a uniform height and the coupling cap may have an upper portion inclined forward such that the cup is inclined forward.

In one embodiment of the present invention, the support may have a connection hole formed through a joint between the coupling cap and the cup, the connection hole being provided therein with a sealing member having a first flange tightly contacting one surface of the coupling cap and a second flange tightly contacting one surface of the cup and formed at a center thereof with a contact hole through which the second guide passes.

In one embodiment of the present invention, the airbag may include: an inner portion having a mounting ring coupled to the mounting groove, the inner portion extending in a longitudinal direction of the coupling cap to surround the coupling cap; a first inflatable portion connected to the inner portion and surrounding some portion of an outer surface of the inner portion, the first inflatable portion being inflated with air supplied thereinto to seal the interior of the vagina; and a second inflatable portion connected to the inner portion and surrounding the other portion of the outer surface of the inner portion, the second inflatable portion being inflated with air supplied thereinto to seal the interior of the vagina independently of the first inflatable portion.

In one embodiment of the present invention, the head may include: an extension bar extending from one end of the second guide at a predetermined angle with respect to the second guide; a first rotating portion hingedly coupled at one end thereof to one end of the extension bar and having a seating groove formed in a longitudinal direction thereof, the first rotating portion being pivoted in the direction of an imaginary extension line of the second guide; a second rotating portion hingedly coupled at one end thereof to the other end of the first rotating portion and corresponding in shape to the seating groove; and a ring portion coupled to at one end thereof the other end of the second rotating portion and the other end of the ring portion surrounds an outer surface of the extension bar, the ring portion being moved back and forth in a longitudinal direction of the extension bar upon rotation of the first rotating portion and the second rotating portion.

In one embodiment of the present invention, upon insertion of the head into the uterine corpus through the uterine cervix, the second rotating portion may be inserted into the seating groove and the ring portion may be located at the one end of the extension bar to allow the head to extend in a longitudinal direction of the slider, and, when the head continues to be inserted into the uterine corpus and the other end of the first rotating portion is pressed by the upper portion of the uterine corpus, the second rotating portion and the first rotating portion may be pivoted and the ring portion may be moved in the direction of the other end of the extension bar to allow the extension bar, the first rotating portion, and the second rotating portion to contact the uterine corpus.

In one embodiment of the present invention, when the other end of the first rotating portion is pressed by the uterine corpus upon withdrawal of the head from the uterine corpus, the first rotating portion may be pivoted such that the second rotating portion is inserted into the seating groove and the ring portion is located at the one end of the extension bar to allow the extension bar, the first rotating portion, and the second rotating portion to extend in the longitudinal direction of the slider.

In one embodiment of the present invention, the extension bar may have a smaller diameter than the second guide and may have a fifth stopper formed at the one end thereof and having a larger diameter than the extension bar to allow the ring portion to be caught and stopped by the second guide and the fifth stopper.

Advantageous Effects

According to the embodiments of the present invention, when the second rotating portion is inserted into the seating groove of the first rotating portion and the ring portion is located at one end of the extension bar, the head can extend in an almost straight line in the longitudinal direction of the slider, whereby insertion of the head into the uterus and withdrawal of the head from the uterus can be facilitated.

In addition, according to the embodiments of the present invention, the second rotating portion and the first rotating portion can be pivoted inside the uterus and the ring portion can be moved in the direction of the other end of the extension bar such that the extension bar, the first rotating portion, and the second rotating portion can contact the uterine corpus. That is, the head can be changed into an inverted triangle shape. In this way, the head can be secured in place corresponding to the shape of the uterine cavity, that is, a lower portion of the uterus, thereby allowing rotation of the uterus as well as front-and-back and side-to-side movement of the uterus during surgery.

Further, according to the embodiments of the present invention, the second inflatable portion constituting the airbag can be operated independently of the first inflatable portion. Accordingly, even when one of the first inflatable portion and the second inflatable portion bursts, the other one can prevent gas leakage.

It will be understood that advantageous effects of the present invention are not limited to the above and include any advantageous effects conceivable from features disclosed in the detailed description of the present invention or the appended claims.

DESCRIPTION OF DRAWINGS

FIG. 1 is a perspective view of a uterine manipulator according to one embodiment of the present invention.

FIG. 2 is an exploded perspective view of the uterine manipulator according to the embodiment, mainly illustrating a main body of the uterine manipulator.

FIG. 3 is a perspective view of the uterine manipulator according to the embodiment, mainly illustrating a mount and an adjuster of the uterine manipulator.

FIG. 4 is an exploded perspective view of the uterine manipulator according to the embodiment, mainly illustrating the adjuster of the uterine manipulator.

FIG. 5 is an exploded perspective view of the uterine manipulator according to the embodiment, mainly illustrating a slider of the uterine manipulator.

FIG. 6 is a perspective view of a head of the uterine manipulator according to the embodiment.

FIG. 7 is a schematic view illustrating exemplary operation of the head of the uterine manipulator according to the embodiment.

FIG. 8 is a perspective view of a support of the uterine manipulator according to the embodiment.

FIG. 9 is a sectional perspective view of the support of the uterine manipulator according to the embodiment.

FIG. 10 is a perspective view of the support of the uterine manipulator according to another embodiment of the present invention.

FIG. 11 is a perspective view of the support of the uterine manipulator according to a further embodiment of the present invention.

FIG. 12 is a sectional view taken along line A-A' of FIG. 11.

FIG. 13 is a sectional perspective view of the uterine manipulator according to the embodiment, mainly illustrating an airbag of the uterine manipulator.

FIG. 14 is a sectional schematic view of the uterine manipulator according to the embodiment, mainly illustrating a first adapter of the uterine manipulator.

FIG. 15 is a schematic view illustrating exemplary use of the uterine manipulator according to the embodiment.

<List of Reference numerals>

| | |
|---|---|
| 10: Vagina | 11: Uterine cervix |
| 12: Uterine corpus | 100: Main body |
| 120: First guide | 130: Guide rail |
| 200: Mount | 300, 300a, 300b: Support |
| 310: Coupling cap | 320: Cup |
| 321: Stepped portion | 330: Guide ring |
| 350: Sealing member | 400: Slider |
| 420: Second guide | 430: Securing portion |
| 500: Adjuster | 510: Sliding block |
| 520: Adjustment lever | 600: Head |
| 610: Extension bar | 620: First rotating portion |
| 630: Second rotating portion | 631: Ring portion |
| 700: Airbag | 710: Inner portion |
| 720: First inflatable portion | 730: Second inflatable portion |

BEST MODE

Reference will now be made in detail to various embodiments, examples of which are illustrated in the accompanying drawings. It should be understood that the present invention may be embodied in different ways and is not limited to the following embodiments. In the drawings, portions irrelevant to the description will be omitted for clarity. Like components will be denoted by like reference numerals throughout the specification.

Throughout the specification, when an element or layer is referred to as being "on," "connected to," or "coupled to' another element or layer, it may be directly on, connected to, or coupled to the other element or layer or intervening elements or layers may be present. In addition, unless stated otherwise, the term "includes" should be interpreted as not excluding the presence of other components than those listed herein.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Hereinafter, embodiments of the present invention will be described in detail with reference to the accompanying drawings.

FIG. 1 is a perspective view of a uterine manipulator according to one embodiment of the present invention.

Referring to FIG. 1, the uterine manipulator is adapted to be inserted into a woman's vagina 10 (see FIG. 15) and the uterine cervix 11 (see FIG. 15) and corpus 12 (see FIG. 15) connected to the vagina 10 to manipulate the uterus in laparoscopic surgery.

The uterine manipulator may include a main body 100, a mount 200, a support 300, a slider 400, an adjuster 500, a head 600, and an airbag 700.

The main body 100 may extend in one direction to be inserted into the vagina 10. The main body 100 may be coupled at one end thereof to a handle 140.

The mount 200 may be disposed at the other end of the main body 100. The support 300 may be disposed on the mount 200 to be inserted into the vagina 10 to support the uterine cervix 11.

The slider 400 may pass through the mount 200 to be connected at one end thereof to the main body 100. The slider 400 may extend in one direction to be inserted into the uterine corpus 12.

The adjuster 500 may be coupled to both the one end of the slider 400 and the main body 100. The adjuster 500 may be moved back and forth in a longitudinal direction of the main body 100 to move the slider 400 back and forth in the longitudinal direction of the main body 100, and may secure the slider 400 to the main body 100 to adjust a length of the slider 400 relative to the main body 100.

The head 600 may be disposed at the other end of the slider 400. The head 600 may be pressed by an upper portion of the uterine corpus 12 to be changed in shape to tightly contact multiple inner points of the uterine corpus 12 upon insertion of the slider 400 into the uterine corpus 12. In addition, the head may be pressed by the uterine cervix 11 to be changed in shape and released from the multiple inner points of the uterine corpus 12 upon withdrawal of the slider 400 from the uterine corpus 12.

The airbag 700 may be coupled to the support 300 and may be inflated with air supplied thereto to seal the interior of the vagina 10.

FIG. 2 is an exploded perspective view of the uterine manipulator according to the embodiment of the present invention, mainly illustrating the main body.

Referring to FIG. 2, the main body 100 may include a first stick 110, a first guide 120, and a guide rail 130.

The first stick 110 may form a body portion of the main body 100 and may extend in one direction.

The first guide 120 may extend to a predetermined length from the first stick 110 in a longitudinal direction of the first stick 110. The first guide 120 may have a rectangular cross-section. The first guide 120 may have a first stopper 121 protruding from one end thereof and a second stopper 122 protruding from the other end thereof.

The guide rail 130 may extend on both side surfaces of the first guide 120 in a longitudinal direction of the first guide 120.

One end of the guide rail 130 may be connected to the second stopper 122. The other end of the guide rail 130 may be separated from the first stopper 121 such that an insertion groove 123 is formed between the other end of the guide rail 130 and the first stopper 121. The insertion groove 123 may be continuous with the first guide 120.

The handle 140 may be coupled to the one end of the main body 100. The handle 140 may have a connection hole 141 therein such that the one end of the main body 100 can be inserted into and coupled to the connection hole 141.

In addition, the handle 140 may have a through-hole 142, whereby the weight of the handle 140 can be reduced. The handle 140 may extend in two opposite directions with respect to the main body 100, whereby force pushing the uterus and force rotating the uterus can be easily transmitted through the handle 140 gripped by a user. The handle 140 may be formed of a metal, such as aluminum, or a sterilizable reinforced resin.

FIG. 3 is a perspective view of the uterine manipulator according to the embodiment, mainly illustrating the mount and the adjuster, FIG. 4 is an exploded perspective view of the uterine manipulator according to the embodiment, mainly illustrating the adjuster, and FIG. 5 is an exploded perspective of the uterine manipulator according to the embodiment, mainly illustrating the slider.

Referring to FIG. 3 to FIG. 5, the mount 200 may include a body block 210, a long groove 211, a guide hole 212, and a recess 213.

The body block 210 may form a body of the mount 200 and may have a coupling groove 214 formed on one surface thereof in a direction parallel to an axial direction of the body block. The coupling groove 214 may receive one end of the first stick 110, whereby the mount 200 can be coupled to the main body 100.

The long groove 211 may be axially formed on an outer surface of the body block 210. The long groove 211 may include a pair of long grooves, which are symmetrical to each other about the center of the body block 210.

The guide hole 212 may be axially formed through the body block 210. The guide hole 212 may correspond in cross-section to a second guide 420 of the slider 400 described below so as to receive the second guide 420 therein. Accordingly, the guide hole 212 can guide movement of the slider 400 while restraining rotation of the slider 400.

The guide hole 212 may be enlarged in a direction from the mount 200 to the handle 140. In this way, after the slider 400 passes through the mount 200, opposite ends of the slider 400 can be moved in a seesaw fashion.

The recess 213 may be formed on the outer surface of the body block 210. The recess 213 may include a pair of recesses, which are symmetrical to each other about the center of the body block 210.

The slider 400 may include a second stick 410, a second guide 420, and a securing portion 430.

The second stick 410 may extend in one direction.

The second guide 420 may be connected to one end of the second stick 410 and may extend to a predetermined length in one direction. The second guide 420 may have a rectangular cross-section.

The securing portion 430 may be formed at the other end of the second stick 410. The securing portion 430 may correspond in cross-section to the first guide 120. In addition, the securing portion 430 may have a third stopper 431 protruding from one end thereof. The third stopper 431 may correspond to the first stopper 121. Further, the securing portion 430 may include a fourth stopper 431 protruding from the other end thereof.

Accordingly, when the securing portion 430 is aligned with the first guide 120, the securing portion 430 can be continuous with both an outer surface of the first guide 120 and the insertion groove 123.

The fourth stopper 432 may be tapered so as to be easily inserted into the guide hole 212.

The adjuster 500 may include a sliding block 510 and an adjustment lever 520.

The sliding block 510 may have a first slit 511, a second slit 512, and a third slit 513.

The first slit 511 may correspond in cross-section to the first guide 120. The first slit 511 may be formed on one surface of the sliding block 510 and may receive the first guide 120. The first guide 120 may tightly contact the first slit 511 upon insertion into the first slit 511.

The second slit 512 may extend from the first slit 511 and may correspond in cross-section to the securing portion 430 of the slider 400. The second slit 512 may receive the securing portion 430. The securing portion 430 may tightly contact the second slit 512 upon insertion into the second slit 512.

The third slit 513 may be formed at both sides of an inner surface of the first slit 511 to correspond in cross-section to the guide rail 130. The third slit 513 may receive the guide rail 130. The guide rail 130 may tightly contact the third slit 513 upon insertion into the third slit 513.

The securing portion 430 and the insertion groove 123 may be sequentially inserted into and coupled to the sliding block 510, whereby the main body 100 and the slider 400 can be coupled to the adjuster 500. After the main body 100 and the slider 400 are coupled to the adjuster 500 such that the securing portion 430 is coupled to the second slit 512, the first guide 120 is coupled to the first slit 511, and the guide rail 130 is coupled to the third slit 513, the adjuster 500 can be moved back and forth along the first guide 120.

When the adjuster 500 is moved from the first stopper 121 towards the second stopper 122 along the first guide 120, the fourth stopper 432 is caught by the sliding block 510 to allow the slider 400 to be moved together with the adjuster 500, causing the stroke of the slider 400 to be shortened. On the other hand, when the adjuster 500 is moved from the second stopper 122 towards the first stopper 121 along the first guide 120, the third stopper 431 is caught by the sliding block 510 to allow the slider 400 to be moved together with the adjuster 500, causing the stroke of the slider 400 to be lengthened. That is, the adjuster 500 can adjust the stroke of the slider 400 by moving the slider 400 through back-and-forth movement along the first guide 120.

In addition, the sliding block 510 may be formed therethrough with an engagement hole 514 connected to the second slit 512. The engagement hole 514 may have a first thread 515 formed on an inner surface thereof.

The adjustment lever 520 may have a pressing member 521. The pressing member may have a second thread 522 formed on an outer surface thereof. The pressing member 521 may be screwed to the engagement hole 514.

The pressing member 521 may be coupled to the engagement hole 514 and may extend inside the second slit 512 to push the securing portion 430. When the pressing member 521 pushes the securing portion 430, the guide rail 130 can be tightly coupled to the third slit 513 to secure the slider 400.

The adjuster 500 may be removed from the slider 400 and the main body 100 to be easily cleaned and sterilized after surgery. The adjuster 500 may be formed of a metal, such as stainless steel, or a reinforced resin.

FIG. 6 is a perspective view of the head of the uterine manipulator according to the embodiment and FIG. 7 is a schematic view illustrating exemplary operation of the head of the uterine manipulator according to the embodiment.

Referring to FIG. 6 and FIG. 7, the head 600 may include an extension bar 610, a first rotating portion 620, and a second rotating portion 630.

The extension bar 610 may extend from one end of the second guide 420 at a predetermined angle θ with respect to the second guide 420.

The extension bar 610 may have a smaller diameter than the second guide 420 and may be formed at one end thereof with a fifth stopper 611 having a larger diameter than the extension bar.

One end of the first rotating portion 620 may be hingedly coupled to the one end of the extension bar 610 to be pivoted about the one end of the extension bar 610. The first rotating portion 620 may be pivoted in the direction of an imaginary extension line L of the second guide 420. In addition, the first rotating portion 620 may have a seating groove 621 formed in a longitudinal direction thereof.

The second rotating portion 630 may be hingedly coupled at one end thereof to the other end of the first rotating portion 620 to be pivoted about the one end of the first rotating portion 620. In addition, the second rotating portion 630 may be coupled at the other end thereof to a ring portion 631.

The ring portion 631 may surround an outer surface of the extension bar 610 and may be moved back and forth in a longitudinal direction of the extension bar 610 upon rotation of the first rotating portion 620 and the second rotating portion 630. The ring portion 631 may be caught and stopped by the second guide 420 and the fifth stopper 611 to restrain rotation of the first rotating portion 620 and the second rotating portion 630 (see FIG. 6(b)).

The second rotating portion 630 may correspond in shape to the seating groove 621 of the first rotating portion 620. Accordingly, when the second rotating portion 630 is pivoted in the direction of the first rotating portion 620, the second rotating portion 630 is inserted into the seating groove 621 of the first rotating portion 620 and the first rotating portion 620 and the second rotating portion 630 are moved to a position substantially in line with the extension bar 610, whereby the extension bar 610, the first rotating portion 620, and the second rotating portion 630 can extend in a longitudinal direction of the second guide 420 (see FIG. 6(a)).

Referring to FIG. 7, upon insertion of the head 600 into the uterine corpus 12 through the uterine cervix 11, the second rotating portion 630 is inserted into the seating groove 621 and the ring portion 631 is located at the one end of the extension bar 610, that is, at the fifth stopper 611, whereby the head 600 can extend in the longitudinal direction of the slider 400. That is, the head 600 can have an almost straight line shape to be easily inserted into the uterine corpus.

In addition, when the head 600 continues to be inserted into the uterine corpus and the other end of the first rotating portion 620 is pressed by an upper portion A of the uterine corpus 12, the second rotating portion 630 and the first rotating portion 620 are pivoted and the ring portion 631 is moved in the direction of the other end of the extension bar 610, whereby the head 600 can be changed into an inverted triangle shape corresponding to the shape of the lower portion of the uterus inside the uterine corpus. Accordingly, an upper surface of the first rotating portion 620 can contact an upper portion of the uterus and a lower portion of the head 600 can tightly contact the lower portion of the uterus. Here, the extension bar 610, the first rotating portion 620, and the second rotating portion 630 can contact multiple points B, C on the uterine corpus 12. In this way, the shape of the head 600 can be locked and maintained corresponding to the shape of the uterine cavity, thereby allowing rotation of the uterus as well as front-and-back and side-to-side movement of the uterus during surgery.

Further, when the other end of the first rotating portion 620 is pressed by the uterine corpus 12 upon withdrawal of the head 600 from the uterine corpus, the first rotating portion 620 are pivoted such that the second rotating portion 630 is inserted into the seating groove 621 of the first rotating portion 620 and the ring portion 631 is located at the fifth stopper 611 of the extension bar 610, whereby the extension bar 610, the first rotating portion 620, and the second rotating portion 630 can extend in the longitudinal direction of the slider 400. That is, the head 600 can be returned to an almost straight line shape so as to be easily withdrawn from the uterine corpus, like when the head 600 is inserted into the uterine corpus.

FIG. 8 is a perspective view of the support of the uterine manipulator according to the embodiment, and FIG. 9 is a sectional perspective view of the support of the uterine manipulator according to the embodiment.

Referring to FIG. 8 and FIG. 9, the support 300 may include a coupling cap 310 and a cup 320.

The coupling cap 310 may be formed on an inner surface thereof with a long protrusion 311 corresponding to the long groove 211 and a coupling protrusion 312 corresponding to the recess 213. Accordingly, the mount 200 can be securely coupled to the inner surface of the coupling cap 310 to be prevented from being rotated inside the coupling cap 310.

In addition, the coupling cap 310 may have a mounting groove 313 circumferentially formed on an outer surface thereof.

The cup 320 may be connected to the coupling cap 310 and may receive the uterine cervix 11 therein. The cup 320 may have an elliptical shape and may be higher at a rear portion thereof than at a front portion thereof. That is, the rear portion of the cup 320 may have a greater height than the front portion of the cup 320 such that an upper portion of the cup 320 is inclined forward.

In addition, the cup 320 may have a cut-out groove 323 formed at both sides thereof to allow blood and impurities to be discharged from the cup 320 through the cut-out groove 323 during surgery.

Further, the cup 320 may have a stepped portion 321 circumferentially formed at one end thereof and having a uniform height. The stepped portion 321 allows a cutting instrument used to cut the vagina 10 to be moved therealong. In this way, the cutting instrument can be moved without slipping.

In addition, the coupling cap 310 may have a coupling hole 314 formed therethrough. The coupling hole 314 may include a pair of coupling holes, wherein the pair of coupling holes may be symmetrical to each other about a center of the coupling cap 310. The coupling hole 314 may be coupled to a tenaculum. The support 300 can be easily withdrawn through the vagina 10 by coupling the tenaculum inserted into the vagina 10 to the coupling hole 314, followed by pulling the tenaculum. The support 300 may be formed of a reinforced resin.

Further, a connection hole 322 may be formed at a joint between the coupling cap 310 and the cup 320. A sealing member 350 may be disposed in the connection hole 322.

The sealing member 350 may have a first flange 351 and a second flange 352.

The first flange 351 may tightly contact one surface of the coupling cap 310, and the second flange 352 may tightly contact one surface of the cup 320. The second flange 352 may have a contact hole 353 formed through a center thereof and allowing the second guide 420 to pass therethrough. The contact hole 353 may tightly contact the second guide 420.

The sealing member 350 may be formed of silicone and may prevent gas leakage during surgery.

FIG. 10 is a perspective view of the support of the uterine manipulator according to another embodiment of the present invention. A support according to this embodiment may further include a guide ring. Since the other parts of the support according to this embodiment are the same as those of the support according to the above embodiment, detailed description thereof will be omitted.

Referring to FIG. 10, the support 300a according to this embodiment may further include a guide ring 330. The guide ring 330 may circumferentially protrude from a lower outer surface of the cup 320. The guide ring 330 may have the same function as the stepped portion 321. That is, the guide ring 330a allows a cutting instrument used to cut the vagina to be moved therealong. Accordingly, the cutting instrument can be moved without slipping.

Referring to FIG. 15, in general hysterectomy, the vagina 10 is cut at a position corresponding to the uterine cervix 11. In this case, cutting of the vagina 10 is thus performed using the stepped portion 321 of the cup 320, and the position OL1 at which the vagina 10 is cut may correspond to the position of the stepped portion 321.

On the other hand, for cervical cancer, the vagina 10 is cut at a position below the uterine cervix 11. In this case, cutting of the vagina 10 is thus performed using the guide ring 330. Although FIG. 15 shows an example in which the support 300 of FIG. 8 is used, when the support 300a according to this embodiment is used, the position OL2 at which the vagina 10 is cut may correspond to the position of the guide ring 330.

For cervical cancer, the vagina is generally cut at a position about 2 cm below a position at which the vagina is cut in hysterectomy. Accordingly, in this embodiment, the guide ring 330 may be separated a distance H of 1.5 cm to 2.5 cm from the stepped portion 321.

FIG. 11 shows perspective views of the support of the uterine manipulator according to a further embodiment of the present invention, wherein FIG. 11(a) is a top-perspective view of the support and FIG. 11(b) is a bottom-perspective view of the support. FIG. 12 is a sectional view taken along line A-A' of FIG. 11. In this embodiment, a cup is generally inclined and a guide ring is further provided. Since the other parts of the support according to this embodiment are the same as those of the support according to the above embodiment, detailed description thereof will be omitted.

Referring to FIG. 11 and FIG. 12, in this embodiment, a cup 320b may have a uniform height. In addition, a guide ring 330 may circumferentially protrude from a lower outer surface of the cup 320b.

A coupling cap 310b may be inclined forward at an upper portion thereof. Accordingly, the cup 320b may also be inclined forward. That is, a center line CL2 of the cup 320b may be inclined at a predetermined angle SA with respect to a center line CL1 of the coupling cap 310b.

Referring to FIG. 1, the main body 100 and the slider 400 may have a gently curved profile, which may correspond to the curvature of the uterus and the vagina. In this embodiment, the predetermined angle SA at which the center line CL2 of the cup 320b is inclined with respect to the center line CL1 of the coupling cap 310b may correspond to the curvature of the uterus and the vagina. In this way, the support 300b can guide the main body 100 and the slider 400 to be more stably inserted into the vagina and the uterus during surgery.

Since the cup 320b has a uniform height and the guide ring 330 is formed at the lower end of the cup 320b, as described above, the stepped portion 321 may be separated from the guide ring 330 by the same distance H as in the above embodiment. Here, the distance H may range from 1.5 cm to 2.5 cm.

FIG. 13 is a sectional perspective view of the uterine manipulator according to the embodiment, mainly illustrating the airbag, FIG. 14 is a sectional schematic view of the uterine manipulator according to the embodiment, mainly illustrating a first adapter, and FIG. 15 is a schematic view illustrating exemplary use of the uterine manipulator according to the embodiment.

Referring to FIG. 13 to FIG. 15, the airbag 700 may have an inner portion 710, a first inflatable portion 720, and a second inflatable portion 730.

The inner portion 710 may have a mounting ring 711 coupled to the mounting groove 313 of the support 300, and may extend in the longitudinal direction of the coupling cap 310 to surround the coupling cap 310.

The first inflatable portion 720 may be connected to the inner portion 710 and may surround some portion of an outer surface of the inner portion 710. A first tube 721 may be connected to the first inflatable portion 720, and a first adapter 722 may be connected to one end of the first tube 721. An air supply unit (not shown) may be connected to the first adapter 722 to supply air to the first inflatable portion. The first inflatable portion 720 may be inflated with air supplied from the air supply unit through the first tube 721.

Upon inflation, the first inflatable portion 720 may seal the interior of the vagina 10, thereby preventing gas leakage through the vagina upon cutting the vagina during surgery.

The first adapter 722 may be provided therein with a check valve 723. The check valve 723 may be connected to the air supply unit. The air supply unit may be a syringe. When air is supplied from the air supply unit, the check valve 723 may be opened by air pressure. When air supply from the air supply unit is stopped, the check valve 723 may be closed by air pressure inside the first tube 721.

After the first inflatable portion 720 is inflated, a first stopper 725 may block the check valve 723 to prevent air from being discharged from the first inflatable portion.

The second inflatable portion 730 may be connected to the inner portion 710 and may surround the other portion of the outer surface of the inner portion 710. A second tube 731 may be connected to the second inflatable portion 730 and a second adapter 732 may be connected to one end of the second tube 731. An air supply unit (not shown) may be connected to the second adapter 732 to supply air to the second inflatable portion. The second inflatable portion 730 may be inflated with air supplied from the air supply unit through the second tube 731.

Upon inflation, the first inflatable portion 720 may seal the interior of the vagina 10, thereby preventing gas leakage through the vagina upon cutting the vagina during surgery. The second inflatable portion 730 may be operated independently of the first inflatable portion 720. That is, with the first inflatable portion 720 and the second inflatable portion 730, the airbag 700 may be operated in a fail-safe manner.

With this structure of the airbag, even when one of the first inflatable portion 720 and the second inflatable portion 730 bursts, the other one can prevent gas leakage. The second adapter 732 may also be provided therein with a check valve, as described above. After the second inflatable portion 730 is inflated, a second stopper 735 may block the check valve to prevent air from being discharged from the second inflatable portion.

Although some embodiments have been described herein, it should be understood that these embodiments are provided for illustration only and are not to be construed in any way as limiting the present invention, and that various modifications, changes, alterations, and equivalent embodiments can be made by those skilled in the art without departing from the spirit and scope of the invention. For example, components described as implemented separately may also be implemented in combined form, and vice versa.

The scope of the present invention is indicated by the following claims and all changes or modifications derived from the meaning and scope of the claims and equivalents thereto should be construed as being included in the scope of the present invention.

The invention claimed is:

1. A uterine manipulator adapted to be inserted into a woman's vagina, uterine cervix, and uterine corpus, to manipulate the uterus in laparoscopic surgery, the uterine manipulator comprising:
   a main body coupled at one end thereof to a handle and extending in one direction to be inserted into the vagina;
   a slider connected at one end thereof to the main body and extending in one direction to be inserted into the uterine corpus; and
   a head disposed at a second end of the slider, the head being adapted to be changed into an inverted triangle shape corresponding to a shape of a lower portion of the uterus inside the uterine corpus by being pressed by an upper portion of the uterine corpus upon insertion of the slider into the uterine corpus and being adapted to be returned to a shape that the head has upon insertion into the uterine corpus by being pressed by the uterine cervix upon withdrawal of the slider from the uterine corpus,
   wherein the head comprises:
   an extension bar extending from the second end of the slider at a predetermined angle with respect to the slider;
   a first rotating portion hingedly coupled at one end thereof to one end of the extension bar and having a seating groove formed in a longitudinal direction thereof;
   a second rotating portion hingedly coupled at one end thereof to another end of the first rotating portion and corresponding in shape to the seating groove; and
   a connecting portion coupled at one end thereof to another end of the second rotating portion, and connected at another end thereof to another end of the extension bar.

2. The uterine manipulator according to claim 1, wherein the connecting portion has a ring portion surrounding an outer surface of the extension bar, the connecting portion being moved back and forth in a longitudinal direction of the extension bar upon rotation of the first rotating portion and the second rotating portion.

\* \* \* \* \*